(12) United States Patent
Bektesevic et al.

(10) Patent No.: US 9,359,273 B2
(45) Date of Patent: Jun. 7, 2016

(54) PROCESS FOR PRODUCING 2,3,3,3-TETRAFLUOROPROPENE

(71) Applicant: HONEYWELL INTERNATIONAL INC., Morristown, NJ (US)

(72) Inventors: Selma Bektesevic, Williamsville, NY (US); Daniel C. Merkel, West Seneca, NY (US); Mario Joseph Nappa, Newark, DE (US); Xuehui Sun, Swedesboro, NJ (US); Hsueh Sung Tung, Getzville, NY (US); Haiyou Wang, Amherst, NY (US)

(73) Assignee: HONEYWELL INTERNATIONAL INC., Morristown, NJ (US)

( * ) Notice: Subject to any disclaimer, the term of this patent is extended or adjusted under 35 U.S.C. 154(b) by 0 days.

(21) Appl. No.: 14/351,732

(22) PCT Filed: Oct. 11, 2012

(86) PCT No.: PCT/US2012/059716
§ 371 (c)(1),
(2) Date: Apr. 14, 2014

(87) PCT Pub. No.: WO2013/055894
PCT Pub. Date: Apr. 18, 2013

(65) Prior Publication Data
US 2014/0316170 A1    Oct. 23, 2014

Related U.S. Application Data

(60) Provisional application No. 61/547,169, filed on Oct. 14, 2011, provisional application No. 61/547,249, filed on Oct. 14, 2011.

(51) Int. Cl.
*C07C 17/20* (2006.01)
*C07C 17/25* (2006.01)
*C07C 21/04* (2006.01)
*C07C 17/087* (2006.01)

(52) U.S. Cl.
CPC .............. *C07C 17/20* (2013.01); *C07C 17/087* (2013.01); *C07C 17/25* (2013.01); *C07C 21/04* (2013.01)

(58) Field of Classification Search
CPC ...... C07C 17/20; C07C 17/087; C07C 17/25; C07C 21/04
USPC ........................................ 570/135, 155, 156
See application file for complete search history.

(56) References Cited

U.S. PATENT DOCUMENTS

| | | | |
|---|---|---|---|
| 2,931,840 A | 4/1960 | Marquis | |
| 3,258,500 A | 6/1966 | Swamer et al. | |
| 4,900,874 A | 2/1990 | Ihara et al. | |
| 5,162,594 A | 11/1992 | Krespan | |
| 6,313,360 B1 | 11/2001 | Wilson et al. | |
| 6,720,466 B2 | 4/2004 | Wilson et al. | |
| 7,189,884 B2 * | 3/2007 | Mukhopadhyay et al. ... | 570/160 |
| 7,795,480 B2 | 9/2010 | Merkel et al. | |
| 8,058,486 B2 | 11/2011 | Merkel et al. | |
| 8,084,653 B2 | 12/2011 | Tung et al. | |
| 8,563,789 B2 * | 10/2013 | Elsheikh et al. .............. | 570/160 |
| 2007/0097842 A1 | 5/2007 | Ando et al. | |
| 2009/0030244 A1 | 1/2009 | Merkel et al. | |
| 2009/0240090 A1 | 9/2009 | Merkel et al. | |
| 2010/0331583 A1 | 12/2010 | Johnson et al. | |
| 2011/0087054 A1 | 4/2011 | Tirtowidjojo et al. | |
| 2011/0087055 A1 | 4/2011 | Tirtowidjojo et al. | |
| 2011/0087056 A1 | 4/2011 | Tirtowidjojo et al. | |
| 2011/0155942 A1 | 6/2011 | Pigamo et al. | |
| 2011/0178343 A1 | 7/2011 | Kruper, Jr. et al. | |
| 2012/0022303 A1 | 1/2012 | Nose et al. | |

FOREIGN PATENT DOCUMENTS

| | | |
|---|---|---|
| CN | 1331067 A | 1/2002 |
| CN | 101597209 A | 12/2009 |
| CN | 101955414 A | 1/2011 |
| CN | 102911006 A | 2/2013 |
| EP | 1 153 906 A1 | 11/2001 |
| GB | 1316709 | 10/1971 |
| WO | 2010123148 A1 | 10/2010 |

OTHER PUBLICATIONS

Chinese Office Action and Search Report dated Feb. 28, 2015, issued in Patent Application No. 201280061573.4 (in English and in Chinese).
Database WPI, XP-002738343 dated Jan. 26, 2011, Section Ch., Week 201138, Thomson Scientific.
Extended Supplementary European Search Report dated May 18, 2015 from related European Application No. 12 84 0714.5.

* cited by examiner

*Primary Examiner* — Shailendra Kumar
(74) *Attorney, Agent, or Firm* — Scully Scott Murphy and Presser

(57) ABSTRACT

The present invention relates, in part, to the discovery that the presence of impurities in 1,1,2,3-tetrachloropropene (1230xa) results in catalyst instability during the fluorination of 1230xa to 2-chloro-3,3,3-trifluoropropene. By substantially removing the impurities, it is shown that the catalyst life is extended and results in improved operation efficiency of the fluorination reaction. Such steps similarly result in an overall improvement in the production of certain hydrofluoroolefins, particularly 2,3,3,3-tetrafluoropropene (1234yf).

29 Claims, 8 Drawing Sheets

PROCESS FOR PRODUCING 2,3,3,3-TETRAFLUOROPROPENE

CROSS REFERENCE TO RELATED APPLICATIONS

This application claims is a 371 of PCT/US2012/059716, filed Oct. 11, 2012, and priority of U.S. provisional applications having Ser. Nos. 61/547,249 and 61/547,169, both of which were filed on Oct. 14, 2011, and the contents of both of which are incorporated by reference.

FIELD OF THE INVENTION

The present invention relates to a process for preparing fluorinated organic compounds, more particularly to a process for preparing fluorinated olefins, and even more particularly to a process for producing 2,3,3,3-tetrafluoropropene (HFO-1234yf).

BACKGROUND OF THE INVENTION

As a result of the Montreal protocol phasing out ozone depleting chlorofluorocarbons (FCs) and hydrochlorofluorocarbons (HCFCs), industry has been working for the past few decades to find replacement refrigerants. The use of new hydrofluorocarbons in various products, such as solvents, blowing agents, cleaning agents, aerosol propellants, heat transfer media, dielectrics, fire extinguishants and power cycle working fluids has made hydrofluorocarbons the subject of considerable interest, especially since they have reduced global warming potential (GWP) and reduced ozone depletion potential (ODP). Promising hydrocarbons include hydrofluoroolefins.

Hydrofluoroolefins (HFOs), such as tetrafluoropropenes (including 2,3,3,3-tetrafluoropropene (HFO-1234yf)), are now known to be effective refrigerants, fire extinguishants, heat transfer media, propellants, foaming agents, blowing agents, gaseous dielectrics, sterilant carriers, polymerization media, particulate removal fluids, carrier fluids, buffing abrasive agents, displacement drying agents and power cycle working fluids. Unlike chlorofluorocarbons (CFCs) and hydrochlorofluorocarbons (HCFCs), both of which potentially damage the Earth's ozone layer, HFOs do not contain chlorine and, thus, pose no threat to the ozone layer. In particular, 2,3,3,3-tetrafluoropropene (HFO-1234yf or 1234yf) has been identified as a suitable compound having zero ODP and low GWP. HFO-1234yf has also been shown to be a low global warming compound with low toxicity and, hence, can meet increasingly stringent requirements for refrigerants in mobile air conditioning. Accordingly, compositions containing HFO-1234yf are among the materials being developed for use in many of the aforementioned applications.

Several methods of preparing HFOs, including HFO-1234yf, are known. For example, U.S. Pat. No. 4,900,874 (Ihara et al) describes a method of making fluorine containing olefins by contacting hydrogen gas with fluorinated alcohols. Although this appears to be a relatively high-yield process, commercial scale handling of hydrogen gas at high temperature is hazardous. Also, the cost of commercially producing hydrogen gas, such as building an on-site hydrogen plant, is economically costly.

U.S. Pat. No. 2,931,840 (Marquis) describes a method of making fluorine containing olefins by pyrolysis of methyl chloride and tetrafluoroethylene or chlorodifluoromethane. This process is a relatively low yield process and a very large percentage of the organic starting material is converted to unwanted and/or unimportant byproducts, including a sizeable amount of carbon black which tends to deactivate the catalyst used in the process.

The preparation of HFO-1234yf from trifluoroacetylacetone and sulfur tetrafluoride has been described (See Banks, et al., Journal of Fluorine Chemistry, Vol. 82, Iss. 2, p. 171-174 (1997)). Also, U.S. Pat. No. 5,162,594 (Krespan) discloses a process wherein tetrafluoroethylene is reacted with another fluorinated ethylene in the liquid phase to produce a polyfluoroolefin product.

One method for producing HFO-1234yf uses 1,1,2,3,-tetachloropropene (HFO-1230xa or 1230xa) as a starting material. In a method, HCO-1230xa can be catalytically converted to 2-chloro-3,3,3-trifluoropropene (HCFO-1233xf) in the presence of hydrogen fluoride (HF). HCFO-1233xf can then be converted to HFO-1234yf. One such process for preparing HFO-1234yf is described in U.S. Patent Application No. 2007/097842, the contents of which are incorporated by reference. A process for producing HFO-1234yf is also described in U.S. Pat. Nos. 8,058,486 and 8,084,653, the contents of both of which are incorporated by reference.

One of the major issues discovered in the catalytic conversion of HCO-1230xa to HCFO-1233xf is the degradation and/or deactivation of the catalyst. While not wishing to be bound, it is believed that several factors may contribute to the degradation and/or deactivation of the catalyst, including polymerization within the reactor or coking. Many attempts have been made to address this issue.

U.S. Patent Application Publication No. U.S. 2009/0030244 A1 discloses the use of a stabilizer to prevent polymerization or coking. It has been shown that the use of the stabilizer improves catalyst performance in comparison with catalyzed reactions conducted in the absence of a stabilizer.

U.S. Patent Publication No. US 2011/0155942 A1 discloses the use of a polymerization inhibitor to control polymerization and extend the life of the catalyst. In addition, oxygen is fed to the reactor to extend the catalyst lifetime. For example, in the presence of a polymerization inhibitor, conversion of HCO-1230xa decreased from about 99% to below 50% after running continuously for 100 hours as a result of catalyst deactivation. In the presence of oxygen, the conversion of HCO-1230xa decreased from about 99% to below 50% within 18 hours.

Another process is disclosed in WO 2010/123148 A1, in which catalyst degradation and/or deactivation is avoided by preparing HCFO-1233xf in the absence of a catalyst. This process, however, results in clogging of the reactor due to carbide residue. To remove the carbide residue, oxygen is introduced into the system with the reactants or the reaction is halted to allow oxygen to flow through the system.

Although the use of polymerization inhibitors and supplied oxygen has been suggested for extending catalyst life, these methods are believed to lead to other potential problems. Polymerization inhibitors may have low volatility under the reaction conditions, causing the polymerization inhibitors to plug downstream flow. This build-up of polymerization inhibitors may require more down time of the reactor so that the build-up can be removed. Using supplied oxygen may decrease catalyst activity itself, as well as make purification of the product more difficult. Therefore, the use of polymerization inhibitor(s) or supplied oxygen may pose other issues that affect the efficiency of the reaction.

Thus, there is a need for an economic means of producing hydrofluoroolefins, such as HFO-1234yf, while avoiding the problems discussed hereinabove. The present invention satisfies this need among others.

SUMMARY OF INVENTION

The present invention relates, in part, to the surprising discovery that the presence of impurities in vaporized starting or intermediate feed streams used for the production of HFOs, such as 2,3,3,3-tetrafluoropropene (1234yf), can result in the instability and deactivation of catalysts used in the HFO production process. Accordingly, in one aspect, the present invention provides one or more process steps for substantially removing the impurities from the feed streams so as to prolong the catalyst life and improve the reaction efficiency.

In one aspect, the present invention relates to a feed stock for use in preparing a fluoroolefin, where the feed stock includes a composition of 1,1,2,3-tetrachloropropene that is substantially free of impurities. Such impurities may include, but are not limited to, ionic metals and organic compounds other than 1,1,2,3-tetrachloropropene. One non-limiting embodiment of the ionic metal is iron. The composition of 1,1,2,3-tetrachloropropene may be substantially free of the ionic metal, particularly iron, when such an impurity is present in the composition in an amount less than about 100 ppm, less than about 50 ppm, less than about 20 ppm, or less than about 10 ppm.

In further non-limiting embodiments, the one or more organic compounds other than 1,1,2,3-tetrachloropropene include one or a combination of hexachloroethane, tetrachloropropane, pentachloropropane, dichloropropene, trichloropropene, pentachloropropene, or dichlorobutene. The composition may be substantially free of such impurities when any one or all of the organic compounds are present in the composition in an amount less than 1000 ppm, less than 500 ppm, less than 200 ppm, or less than 100 ppm. Alternatively, the composition is substantially free of such impurities when, collectively, the one or more organic compounds are provided at less than 0.5% (w/w) of the composition, less than 0.3% (w/w) of the composition, or less than 0.1% (w/w) of the composition.

In another aspect, the present invention relates to a method for reducing the impurity content of a 1,1,2,3-tetrachloropropene feed stock by providing a composition including 1,1,2,3-tetrachloropropene and reducing the impurity content of the composition such that it is substantially free of impurities. The impurity content may be reduced using any standard method known in the art, such as but not limited to distillation, including, but not limited to fractional distillation, wherein the 1,1,2,3-tetrachloropropene is separated from the starting composition by distilling. Another method for purifying 1,1,2,3-tetrachloropropene is by subjecting it to chromatography, including, but not limited to column chromatography and HPLC.

In another aspect, the present invention relates to a process for preparing 2-chloro-3,3,3-trifluoropropene by providing a starting composition including at least one compound of formula I

$$CX_2=CCl-CH_2X \qquad (I)$$

wherein X is independently selected from F, Cl, Br, and I, provided that at least one X is not fluorine and wherein the starting composition is substantially free of impurities and contacting said starting composition with a fluorinating agent to produce a final composition comprising 2-chloro-3,3,3-trifluoropropene. In certain embodiments, at least one compound of formula I has at least one X is a chlorine. In further embodiments, at least one compound of formula I has a chlorine at each X position. In even further embodiments, at least one compound of formula I includes 1,1,2,3-tetrachloropropene.

The step of contacting the starting composition with a fluorinating agent may occur in the presence of a catalyst. In one aspect, the contacting step occurs in a vapor phase with or without the presence of a vapor phase catalyst. Vapor phase catalysts used for such a reaction include, but are not limited to, a chromium oxide, a chromium hydroxide, a chromium halide, a chromium oxyhalide, an aluminum oxide, an aluminum hydroxide, an aluminum halide, an aluminum oxyhalide, a cobalt oxide, a cobalt hydroxide, a cobalt halide, a cobalt oxyhalide, a manganese oxide, a manganese hydroxide, a manganese halide, a manganese oxyhalide, a nickel oxide, a nickel hydroxide, a nickel halide, a nickel oxyhalide, an iron oxide, an iron hydroxide, an iron halide, an iron oxyhalide, inorganic salts thereof, fluorinated derivatives thereof and combinations thereof. In certain embodiments, the catalyst includes a chromium oxide, such as, but not limited to, $Cr_2O_3$.

Another aspect of the present invention relates to a process comprising providing HCO-1230xa comprising less than 1% impurities as measured by GC FID area.

Another aspect of the present invention relates to providing HCO-1230xa comprising less than 1% impurities as measured by GC FID area; and contacting the HCO-1230xa with hydrogen fluoride in the gas phase in the presence of a catalyst under conditions sufficient to produce HCFO-1233xf.

Another embodiment comprises:

continuously providing HCO-1230xa, wherein the HCO-1230xa comprises less than about 1% impurities as measured by the area of the impurities in a gas chromatograph from a GC FID, i.e., gas chromatography with flame ionization detection ("GC FID area"); and contacting the HCO-1230xa with hydrogen fluoride in the gas phase in the presence of a catalyst under conditions sufficient to continuously produce HCFO-1233xf for at least 100 hours and at least 90% w/w of the HCO-1230xa is reacted, wherein contacting the HCO-1230xa with hydrogen fluoride is performed in the absence of a polymerization inhibitor.

Another aspect of the present invention comprises:

providing HCO-1230xa comprising less than 1% impurities as measured by GC area;

contacting the HCO-1230xa with hydrogen fluoride in the gas phase in the presence of a catalyst under conditions sufficient to produce HCFO-1233xf; and contacting the HCFO-1233xf with hydrogen fluoride under conditions sufficient to produce HFO-1234yf.

Another aspect of the present invention relates to a process comprising providing HCO-1230xa comprising less than 0.95 mol % impurities as measured by GC area Another aspect of the present invention relates to providing HCO-1230xa comprising less than 0.95 mole % impurities as measured by GC area; and contacting the HCO-1230xa with hydrogen fluoride in the gas phase in the presence of a catalyst under conditions sufficient to produce HCFO-1233xf.

Another embodiment comprises:

continuously providing HCO-1230xa, wherein the HCO-1230xa comprises less than about 0.95 mol % impurities as measured by GC area; and contacting the HCO-1230xa with hydrogen fluoride in the gas phase in the presence of a catalyst under conditions sufficient to continuously produce HCFO-1233xf for at least 100 hours and at least 90% w/w of the HCO-1230xa is reacted, wherein contacting the HCO-1230xa with hydrogen fluoride is performed in the absence of a polymerization inhibitor.

Another aspect of the present invention comprises:
providing HCO-1230xa comprising less than 0.95 mol % impurities as measured by GC area;
contacting the HCO-1230xa with hydrogen fluoride in the gas phase in the presence of a catalyst under conditions sufficient to produce HCFO-1233xf; and
contacting the HCFO-1233xf with hydrogen fluoride under conditions sufficient to produce HFO-1234yf.

In even further aspects, the present invention relates to a process for preparing 2,3,3,3-tetrafluoroprop-1-ene by
a. providing a starting composition including a compound of formula I

$$CX_2=CCl-CH_2X \quad (I)$$

wherein X is independently selected from F, Cl, Br, and I, provided that at least one X is not fluorine and the starting composition is substantially free of impurities;
b. contacting the starting composition with a first fluorinating agent to produce a first intermediate composition including 2-chloro-3,3,3-trifluoropropene and a first chlorine-containing byproduct;
c. contacting the first intermediate composition with a second fluorinating agent to produce a second intermediate composition including 2-chloro-1,1,1,2-tetrafluoropropane; and
d. dehydrochlorinating at least a portion of the 2-chloro-1,1,1,2-tetrafluoropropane to produce a reaction product including 2,3,3,3-tetrafluoroprop-1-ene.

Additional embodiments and advantages to the present invention will be readily apparent to one of skill in the art, based on the disclosure provided herein.

BRIEF DESCRIPTION OF THE DRAWINGS

These and other features, aspects, and advantages of the present invention will become better understood with regard to the following description, appended claims, and accompanying drawings.

DETAILED DESCRIPTION OF THE INVENTION

Figure 1:
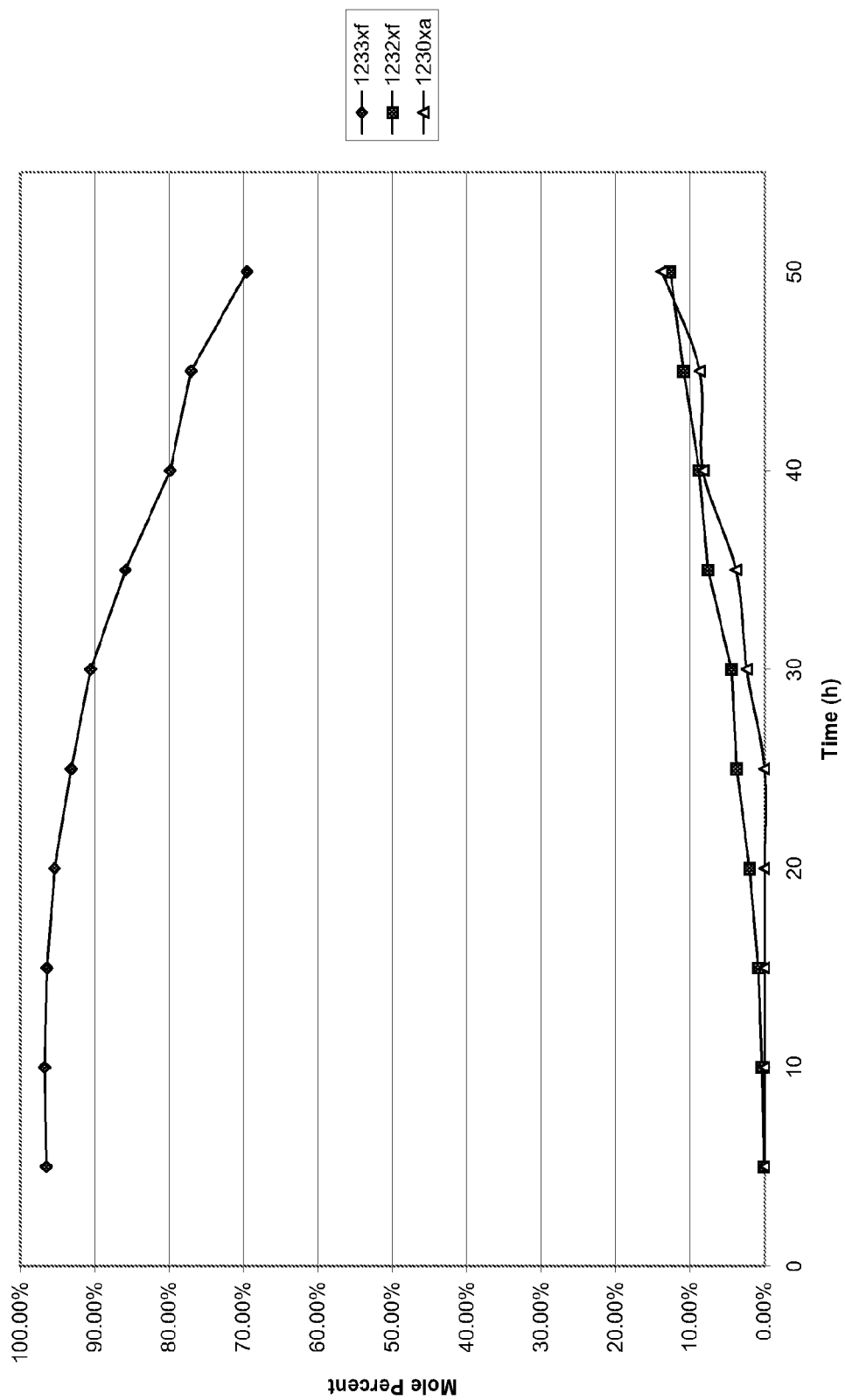
FIG. 1 graphically represents the mole percentage of HCFO-1233xf produced and HCO-1230xa remaining as a function of time resulting from the process conducted in accordance with the procedure of Example 3 herein.

Unless indicated to the contrary, the following terms are defined below.

As used herein, the term "chrome oxide catalyst" and variations thereof, is means a chrome oxide catalyst capable of catalyzing a fluorination reaction. For example, the chrome oxide catalyst catalyzes the fluorination of HCO-1230xa to produce HCFO-1233xf. The chrome oxide catalyst may comprise, for example, a chrome oxide catalyst or a chromium oxyfluoride represented by the formula $Cr_2O_xF_y$, where $x+y/2=3$ and x is an integer 0, 1, 2 or 3 and y is an integer of 0, 1, 2, 3, 4, 5 or 6. The chromium may also be present in oxidation states other than chromium (III), such as 2, 4, 5 or 6.

As used herein, the term "impurity" is used to describe any component, e.g., organic compound or ionic metal but excluding moisture that negatively impacts the overall process described herein for forming HCFO-1233xf, such as catalyst stability or operating ability (e.g., plugging, or corrosion). The amount of impurity present is quantified in either % impurities, ppm, w/w or mole %. It refers to the dry amount of impurity relative to the dry amount of the desired component. The % impurity can be expressed as to the amount of impurity measured as % on the gas chromatograph, in accordance with known procedures. If reference is made to impurity as ppm, it refers to the amount of impurity present in parts per million relative to the composition, unless indicated to the contrary. If the impurity is deemed to be present in % w/w, it means that the impurity is present in a weight percentage of the starting composition. If described in a mol %, this means that the impurity is described as being present in a mole % relative to the mole percentage of HCO-1230xa present in the starting composition. For example, HCO-1230xa comprising less than about 1% impurities comprises less than about 1% of dry amount of any compound other than HCO-1230xa, wherein the percentages are measured as the area in a gas chromatograph (GC) trace according to methods known in the art. If it is stated that the HCO-1230xa comprises less than 1 ppm or 1% (w/w), this means that the amount of compounds other than HCO-1230xa is present in dry amounts as 1 part per million or % by weight of the starting composition, other than HCO-1230xa. Alternatively, if it is stated that the HCO-1230xa comprises 0.1 mole %, this means that the % by mole of the impurity, other than HCO-1230xa in dry amounts relative to the % by mole of HCO-1230xa present in the starting composition of any compound by parts per million or weight, other than HCO 1230xa.

It is to be noted that moisture is not included in the definition of impurity, as defined herein. The effect of moisture on the fluorination reaction of HCO-1230xa to HCFO-1233xf is described in PCT Application No PCT U.S. Ser. No. 12/58152, the contents of which are incorporated by reference.

As used herein, the term "polymerization inhibitor" or "stabilizer" refers to a compound that prevents the polymerization of reactants in the reactor. Polymerization inhibitors include such compounds as p-methoxyphenol, t-amylphenol, d-limonene, quinines, hydroquinones, amines, and mixtures thereof. Other polymerization inhibitors are known to those of ordinary skill in the art.

The term "supplied oxygen" and variations thereof mean oxygen that is added to the reactor during the production of hydrofluoroolefins. The oxygen may be in the form of pure oxygen, oxygen mixed with an inert gas or oxygen present in air. The supplied oxygen may be provided with the reactants or added to the reactor separately. The absence of supplied oxygen does not preclude the presence of oxygen in the reactor. The absence of supplied oxygen means that additional oxygen is not supplied to the reactor.

The terms "degradation" and "deactivation" are used herein to describe the diminishing ability of the catalyst to drive the process. Degradation and deactivation may be measured, for example, by the conversion of the starting product, e.g., how much of the starting material is consumed as a function of time, or by the formation of the desired product over time. For example, in a process wherein HCO-1230xa is converted to HCFO-1233xf, the degradation and/or deactivation of the catalyst may be observed by measuring the percentage of HCO-1230xa that is converted over time, or by measuring the amount of HCFO-1233xf that is produced over time. One of ordinary skill in the art would recognize that other indications could also be used to determine the degradation and/or deactivation of the catalyst.

The term "fluoroolefin", as used herein, refers to an alkene containing at least one fluoro substituent which is useful as a refrigerant, such as 2,3,3,3-tetrafluoropropene), as well as a fluorochloroolefin as an intermediate in the process of in preparing a fluoroolefin such as 2,3,3,3-tetrafluoropropene.

As used herein the term "or" refers to the inclusive "or", so that, for example, a phrase that Z is A or B refers to Z being either A, B or both A and B.

Also, use of "a" or "an" are employed to describe elements and components described herein. This is done merely for convenience and to give a general sense of the scope of the invention. This description should be read to include one or at least one. Moreover, the singular also includes the plural and vice versa unless it is obvious that it is meant otherwise.

Unless otherwise defined, all technical and scientific terms used herein have the same meaning as commonly understood by one of ordinary skill in the art to which this invention belongs. Although methods and materials similar or equivalent to those described herein can be used in the practice or testing of embodiments of the present invention, suitable methods and materials are described below. All publications, patent applications, patents and other references mentioned herein are incorporated in their entirety, unless a particular passage is cited. In case of conflict, the present specification, including definitions, will control.

According to one embodiment, the present invention includes a manufacturing process for making 2,3,3,3-tetrafluoroprop-1-ene using a starting material according to formula I:

  (Formula I)

wherein X is independently selected from F, Cl, Br, and I, provided that at least one X is not fluorine. In certain embodiments, the compound(s) of Formula I contains at least one chlorine, a majority of the Xs as chlorine, or all Xs as chlorine. In certain embodiments, the compound(s) of formula I include 1,1,2,3-tetrachloropropene (1230xa).

The method generally includes at least three reaction steps. In the first step, a starting composition of Formula I (such as 1,1,2,3-tetrachloropropene) is reacted with anhydrous HF in a first vapor phase reactor (fluorination reactor) to produce a mixture of 2-chloro-3,3,3-trifluoropropene (1233xf) and HCl. In certain embodiments, the reaction occurs in the vapor phase in the presence of a vapor phase catalyst, such as, but not limited to, a fluorinated chromium oxide. The catalyst may (or may not) have to be activated with anhydrous hydrogen fluoride HF (hydrogen fluoride gas) before use depending on the state of the catalyst.

While fluorinated chromium oxides are disclosed as the vapor phase catalyst, the present invention is not limited to this embodiment. Any fluorination catalysts known in the art may be used in this process. Suitable catalysts include, but are not limited to chromium, aluminum, cobalt, manganese, nickel and iron oxides, hydroxides, halides, oxyhalides, inorganic salts thereof and their mixtures and any one of which may be optionally fluorinated. In one embodiment, the catalyst is chrome oxide, such as for example, $Cr_2O_3$. Co-catalysts may also be present. Combinations of catalysts suitable for the present invention nonexclusively include $Cr_2O_3$, $FeCl_3/C$, $Cr_2O_3/Al_2O_3$, $Cr_2O_3/AlF_3$, $Cr_2O_3/carbon$, $CoCl_2/Cr_2O_3/Al_2O_3$, $NiCl_2/Cr_2O_3/Al_2O_3$, $CoCl_2/AlF_3$, $NiCl_2/AlF_3$ and mixtures thereof. In one embodiment, the chrome oxide is present with a co-catalyst for fluorination reaction. Chromium oxide/aluminum oxide catalysts are described in U.S. Pat. No. 5,155,082 which is incorporated herein by reference. Chromium catalysts are also described in U.S. Pat. No. 3,258,500, the contents of which are also incorporated by reference. In another embodiment, Chromium (III) oxides such as crystalline chromium oxide or amorphous chromium oxide are used as catalysts, while in another aspect of the present invention, the catalyst for this fluorination step is amorphous chromium oxide. One such chromium oxide catalyst that is used in the first fluorination step is the activated chromium oxide gel catalyst, described in U.S. Pat. No. 3,258,500. Chromium oxide ($Cr_2O_3$) is a commercially available material which may be purchased in a variety of particle sizes.

The chrome oxide catalyst may be a high surface area chrome oxide. In at least one embodiment, the chrome oxide catalyst has a surface area of at least 60 $m^2/g$. In other embodiments, the chrome oxide catalyst may have a surface area of at least 100 $m^2/g$. In at least one embodiment, the surface area of the chrome oxide catalyst may range from about 60 $m^2/g$ to about 400 $m^2/g$. in another embodiment from about 100 $m^2/g$ to about 300 $m^2/g$. Other chrome oxide catalysts may have surface areas higher or lower than these examples.

Fluorination catalysts having a purity of at least 98% are preferred. The fluorination catalyst is present in an excess but in at least an amount sufficient to drive the reaction.

Prior to the reaction, the compound of formula I, particularly when it is 1230xa, is first purified to form a starting feed stream that is substantially free of impurities. It has been surprisingly discovered that, during the fluorination of 1230xa to 1233xf, even a small amount of certain impurities in the reactor feed, particularly in the 1230xa feed stock, have a significant negative impact on (a) the stability of the fluorination catalyst and (b) the resulting reaction product stream. Accordingly, the instant invention, at least in part, relates to methods of improving the catalyst stability.

As used herein, the terms "impurity" or "impurities," include any chemical compound, particularly a halocarbon-based compound, within the 1230xa stream that interferes with the stability of the fluorination catalyst or otherwise reduces the conversion rate and/or selectivity of 1230xa to 1233xf. Non-limiting examples of these impurities include ionic metals such as Fe, chlorinated alkanes or chlorinated alkenes (collectively designated as underchlorinates) such as trichloropropane, dichloropropene, monochoropropane, hexachloroethane, tetrachloropropane, pentachloropropane, dichloropropene, trichloropropene, pentachloropropene, hexachlorohexadiene, dichlorobutene, and the like. While not intending to be bound by theory, it is believed that the impurities, including the 3-carbon alkanes containing less than 5 or less chlorine atoms and/or the 3-carbon alkenes containing less than 4 chlorine atoms and/or the 2-carbon alkanes containing 4 or few chlorine atoms and/or 2-carbon alkenes containing 3 or fewer chlorine atoms, such as, but not limited to hexachloroethane, tetrachloropropane, dichloropropene, and trichloropropene are particularly undesirable because they form oligomers in reactor and/or tend to deposit on catalyst surface, and as a result, may contribute to degradation and/or deactivation of the catalysts used in the process. In addition, or as a consequence thereof, the amount of conversion of HCO-1230xa to HCFO-1233xf is decreased. Accordingly, the present invention, at least in part, relates to the methods of improving the fluorination catalyst stability by using high purity feed in the conversion process and also methods of improving the reaction efficiency.

As used herein, the term "substantially free" means that impurities in the feed stream are removed in a sufficient amount to provide a measurable improvement in fluorination catalyst stability or otherwise improve the conversion rate of the compound of formula I and/or the selectivity of 1230xa to 1233xf. The amount of impurities present in the starting composition in the feed stream comprised of 1,1,2,3-tetrachloropropene when it is substantially free of impurities can be expressed in various ways, such as ppm of impurities present, weight percentage of the impurities relative to the weight of the composition comprised of 1,1,2,3-tetrachloropropene, the mole % of the moles of impurities present relative to the moles of 1,1,2,3-tetrachloropropene present, or the amount of impurities present relative to the amount of 1,1,2,3-tetrachloropropene, as measured by GC (FID) area by standard techniques known in the art. For example, the 1,1,2,3-tetrachloropropene is substantially free of impurities when the HCO-1230xa contains less than 1% impurities and in another embodiment, less than 0.9% impurities, as measured by GC (FID) area using techniques known in the art. Other embodiments include that the HCO-1230xa is substantially free of impurities when it contains less than 0.75% impurities, in another embodiment, less than 0.5% impurities and in a further embodiment, less than 0.2% or less than 0.1% impurities, as measured by GC (FID) area.

In another embodiment, the 1,1,2,3-tetrachloropropene is substantially free of impurities when the HCO-1230xa contains less than 1 mol % impurities and in another embodiment, less than 0.9 mol % impurities. Other embodiments include that the HCO-1230xa is substantially free of impurities when it contains less than 0.75 mol % impurities, in another embodiment, less than 0.5 mol % impurities and in a further embodiment, less than 0.2 mol %, and in another embodiment less than 0.1 mol % impurities.

When the impurity is ionic iron, for example, the feed stream may be "substantially free" of this impurity when it is present in the feed stream in an amount of less than about 100 ppm, less than about 50 ppm, less than about 20 ppm, or less than about 10 ppm. In an aspect, the ionic metal, for example iron, is present in an amount of 100 ppm, 99 ppm, 98 ppm, 97 ppm, 96 ppm, 95 ppm, 94 ppm, 93 ppm, 92 ppm, 91 ppm, 90 ppm, 89 ppm, 88 ppm, 87 ppm, 86 ppm, 85 ppm, 84 ppm, 83 ppm, 82 ppm, 81 ppm, 80 ppm, 79 ppm, 78 ppm, 77 ppm, 76 ppm, 75 ppm, 74 ppm, 73 ppm, 72 ppm, 71 ppm, 70 ppm, 69 ppm, 68 ppm, 67 ppm, 66 ppm, 65 ppm, 64 ppm, 63 ppm, 62 ppm, 61 ppm, 60 ppm, 59 ppm, 58 ppm, 57 ppm, 56 ppm, 55 ppm, 54 ppm, 53 ppm, 52 ppm, 51 ppm, 50 ppm, 49 ppm, 48 ppm, 47 ppm, 46 ppm, 45 ppm, 44 ppm, 43 ppm, 42 ppm, 41 ppm, 40 ppm, 39 ppm, 38 ppm, 37 ppm, 36 ppm, 35 ppm, 34 ppm, 33 ppm, 32 ppm, 31 ppm, 30 ppm, 29 ppm, 28 ppm, 27 ppm, 26 ppm, 25 pm, 24 ppm, 23 ppm, 22 ppm, 21 ppm, 20 ppm, 19 ppm, 18 ppm, 17 ppm, 16 ppm, 15 ppm, 14 ppm, 13 ppm, 12 ppm, 11 ppm, 10 ppm, 9 ppm, 8 ppm, 7 ppm, 6 ppm, 5 ppm, 4 ppm, 3 ppm, 2 ppm, 1 ppm, or 0 ppm. When the impurity is one or more of the organic compounds provided herein, particularly hexachloroethane, tetrachloropropane, dichloropropene, and/or trichloropropene, the feed stream may be "substantially free" of these impurities when they are individually provided at less than 1000 ppm, less than 500 ppm, less than 200 ppm, or less than 100 ppm. In an aspect of the present invention, these impurities are present in an amount of 500 ppm, 499 ppm, 498 ppm, 497 ppm, 496 ppm, 495 ppm, 494 ppm, 493 ppm, 492 ppm, 491 ppm, 490 ppm, 489 ppm, 488 ppm, 487 ppm, 486 ppm, 485 ppm, 484 ppm, 483 ppm, 482 ppm, 481 ppm, 480 ppm, 479 ppm, 478 ppm, 477 ppm, 476 ppm, 475 ppm, 474 ppm, 473 ppm, 472 ppm, 471 ppm, 470 ppm, 469 ppm, 468 ppm, 467 ppm, 466 ppm, 465 ppm, 464 ppm, 463 ppm, 462 ppm, 461 ppm, 460 ppm, 459 ppm, 458 ppm, 457 ppm, 456 ppm, 455 ppm, 454 ppm, 453 ppm, 452 ppm, 451 ppm, 450 ppm, 449 ppm, 448 ppm, 447 ppm, 446 ppm, 445 ppm, 444 ppm, 443 ppm, 442 ppm, 441 ppm, 440 ppm, 439 ppm, 438 ppm, 437 ppm, 436 ppm, 435 ppm, 434 ppm, 433 ppm, 432 ppm, 431 ppm, 430 ppm, 429 ppm, 428 ppm, 427 ppm, 426 ppm, 425 pm, 424 ppm, 423 ppm, 422 ppm, 421 ppm, 420 ppm, 419 ppm, 418 ppm, 417 ppm, 416 ppm, 415 ppm, 414 ppm, 413 ppm, 412 ppm, 411 ppm, 410 ppm, 409 ppm, 408 ppm, 407 ppm, 406 ppm, 405 ppm, 404 ppm, 403 ppm, 402 ppm 401 ppm, 400 ppm, 399 ppm, 398 ppm, 397 ppm, 396 ppm, 395 ppm, 394 ppm, 393 ppm, 392 ppm, 391 ppm, 390 ppm, 389 ppm, 388 ppm, 387 ppm, 386 ppm, 385 ppm, 384 ppm, 383 ppm, 382 ppm, 381 ppm, 380 ppm, 379 ppm, 378 ppm, 377 ppm, 376 ppm, 375 ppm, 374 ppm, 373 ppm, 372 ppm, 371 ppm, 370 ppm, 369 ppm, 368 ppm, 367 ppm, 366 ppm, 365 ppm, 364 ppm, 363 ppm, 362 ppm, 361 ppm, 360 ppm, 359 ppm, 358 ppm, 357 ppm, 356 ppm, 355 ppm, 354 ppm, 353 ppm, 352 ppm, 351 ppm, 350 ppm, 349 ppm, 348 ppm, 347 ppm, 346 ppm, 345 ppm, 344 ppm, 343 ppm, 342 ppm, 341 ppm, 340 ppm, 339 ppm, 338 ppm, 337 ppm, 336 ppm, 335 ppm, 334 ppm, 333 ppm, 332 ppm, 331 ppm, 330 ppm, 329 ppm, 328 ppm, 327 ppm, 326 ppm, 325 pm, 324 ppm, 323 ppm, 322 ppm, 321 ppm, 320 ppm, 319 ppm, 318 ppm, 317 ppm, 316 ppm, 315 ppm, 314 ppm, 313 ppm, 312 ppm, 311 ppm, 310 ppm, 309 ppm, 308 ppm, 307 ppm, 306 ppm, 305 ppm, 304 ppm, 303 ppm, 302 ppm, 301 ppm, 300 ppm, 299 ppm, 298 ppm, 297 ppm, 296 ppm, 295 ppm, 294 ppm, 293 ppm, 292 ppm, 291 ppm, 290 ppm, 289 ppm, 288 ppm, 287 ppm, 286 ppm, 285 ppm, 284 ppm, 283 ppm, 282 ppm, 281 ppm, 280 ppm, 279 ppm, 278 ppm, 277 ppm, 276 ppm, 275 ppm, 274 ppm, 273 ppm, 272 ppm, 271 ppm, 270 ppm, 269 ppm, 268 ppm, 267 ppm, 266 ppm, 265 ppm, 264 ppm, 263 ppm, 262 ppm, 261 ppm, 260 ppm, 259 ppm, 258 ppm, 257 ppm, 256 ppm, 255 ppm, 254 ppm, 253 ppm, 252 ppm, 251 ppm, 250 ppm, 249 ppm, 248 ppm, 247 ppm, 246 ppm, 245 ppm, 244 ppm, 243 ppm, 242 ppm, 241 ppm, 240 ppm, 239 ppm, 238 ppm, 237 ppm, 236 ppm, 235 ppm, 234 ppm, 233 ppm, 232 ppm, 231 ppm, 230 ppm, 229 ppm, 228 ppm, 227 ppm, 226 ppm, 225 pm, 224 ppm, 223 ppm, 222 ppm, 221 ppm, 220 ppm, 219 ppm, 218 ppm, 217 ppm, 216 ppm, 215 ppm, 214 ppm, 213 ppm, 212 ppm, 211 ppm, 210 ppm, 209 ppm, 208 ppm, 207 ppm, 206 ppm, 205 ppm, 204 ppm, 203 ppm, 202 ppm, 201 ppm, 200 ppm, 199 ppm, 198 ppm, 197 ppm, 196 ppm, 195 ppm, 194 ppm, 193 ppm, 192 ppm, 191 ppm, 190 ppm, 189 ppm, 188 ppm, 187 ppm, 186 ppm, 185 ppm, 184 ppm, 183 ppm, 182 ppm, 181 ppm, 180 ppm, 179 ppm, 178 ppm, 177 ppm, 176 ppm, 175 ppm, 174 ppm, 173 ppm, 172 ppm, 171 ppm, 170 ppm, 169 ppm, 168 ppm, 167 ppm, 166 ppm, 165 ppm, 164 ppm, 163 ppm, 162 ppm, 161 ppm, 160 ppm, 159 ppm, 158 ppm, 157 ppm, 156 ppm, 155 ppm, 154 ppm, 153 ppm, 152 ppm, 151 ppm, 150 ppm, 149 ppm, 148 ppm, 147 ppm, 146 ppm, 145 ppm, 144 ppm, 143 ppm, 142 ppm, 141 ppm, 140 ppm, 139 ppm, 138 ppm, 137 ppm, 136 ppm, 135 ppm, 134 ppm, 133 ppm, 132 ppm, 131 ppm, 130 ppm, 129 ppm, 128 ppm, 127 ppm, 126 ppm, 125 pm, 124 ppm, 123 ppm, 122 ppm, 121 ppm, 120 ppm, 119 ppm, 118 ppm, 117 ppm, 116 ppm, 115 ppm, 114 ppm, 113 ppm, 112 ppm, 111 ppm, 110 ppm, 109 ppm, 108 ppm, 107 ppm, 106 ppm, 105 ppm 104 ppm 103 ppm, 102 ppm, 101 ppm, 100 ppm, 99 ppm, 98 ppm, 97 ppm, 96 ppm, 95 ppm, 94 ppm, 93 ppm, 92 ppm, 91 ppm, 90 ppm, 89 ppm, 88 ppm, 87 ppm, 86 ppm, 85 ppm, 84 ppm, 83 ppm, 82 ppm, 81 ppm, 80 ppm, 79 ppm, 78 ppm, 77 ppm, 76 ppm, 75 ppm, 74 ppm, 73 ppm, 72 ppm, 71 ppm, 70 ppm, 69 ppm, 68 ppm, 67 ppm, 66 ppm, 65 ppm, 64 ppm, 63 ppm, 62 ppm, 61 ppm, 60 ppm, 59 ppm, 58 ppm, 57 ppm, 56 ppm, 55 ppm, 54 ppm, 53 ppm, 52 ppm, 51 ppm, 50 ppm, 49 ppm, 48 ppm, 47 ppm, 46 ppm, 45 ppm, 44 ppm, 43 ppm, 42 ppm, 41 ppm, 40 ppm, 39 ppm, 38 ppm, 37 ppm, 36 ppm, 35 ppm, 34 ppm, 33 ppm, 32 ppm, 31 ppm, 30 ppm, 29 ppm, 28 ppm, 27 ppm, 26 ppm, 25 pm, 24 ppm, 23 ppm, 22 ppm, 21 ppm, 20 ppm, 19 ppm, 18 ppm, 17 ppm, 16 ppm, 15 ppm, 14 ppm, 13 ppm, 12 ppm, 11 ppm, 10 ppm, 9 ppm, 8 ppm, 7 ppm, 6 ppm, 5 ppm, 4 ppm, 3 ppm, 2 ppm, 1 ppm, or 0 ppm. The feed stream may also be "substantially free" of such organic impurities when they are collectively provided at less than 0.5% (w/w), less than 0.3% (w/w), or less than 0.1% (w/w) of the composition. In an aspect of the present invention, these impurities are present in an amount of 0.5%, 0.49%, 0.48%, 0.47%, 0.46%. 0.45%, 0.44%, 0.43% 0.42%, 0.41%, 0.40%, 0.39%, 0.38%, 0.37%, 0.36%, 0.35%, 0.34%, 0.33%, 0.32%, 0.31%, 0.30%, 0.29%, 0.28%, 0.27%, 0.26%, 0.25%, 0.24%, 0.23%, 0.22%, 0.21%, 0.20%, 0.19%, 0.18%, 0.17%, 0.16%, 0.15%, 0.14%, 0.134%, 0.12%, 0.11%, 0.10%, 0.09%, 0.08%, 0.07%, 0.06%, 0.05%, 0.04%, 0.03%, 0.02%, 0.01%, or 0% (w/w) of the starting composition.

As described herein, it is more efficient if the starting composition contains as little impurity as possible. However, the removal of all of the aforementioned impurities from the starting composition, although desirable, may not be practical, because of other factors, such as time and expense. However, it has been found that it may not be necessary to remove all of these impurities, i.e., it may be acceptable to have a certain amount of impurity present without substantially sacrificing the selectivity and conversion to 2,3,3,3,-tetrafluoropropene and substantially effecting the life of the fluorination catalyst. For example, it has been found that the starting composition can contain as much as 10 ppm of ionic metal, such as iron, and still provide acceptable storage stability and continuous operation without periodic pluggage and/or shutdown. If the impurity is one of the aforementioned organic compounds, the starting composition can contain as much as 3000 ppm of such organic impurities and still provide acceptable on-stream time before regeneration. The impurities present may be measured in the starting composition comprised of 1,1,2,3-tetrachloropropene is effected using techniques known to the skilled artisan. One method is to inject a sample of the starting composition comprised of 1,1,2,3-tetrachloropropene into a GC and compare the areas of the impurities present relative to the area of the 1,1,2,3-tetrachloropropene present in the gas chromatograph, using techniques known to one of ordinary skill in the art.

Any techniques known in art can be used to purify 1230xa raw material. In one embodiment, the purification method includes distillation. To this end, the raw feed stock is distilled using one or more distillation columns or packed towers. While distillation may occur at atmospheric pressure, superatmospheric pressure or under vacuum, in certain embodiments, it is preferably conducted at a pressure of less than about 300 psig. In another method, the 1230xa raw material is purified using fractional distillation. In still another method, the 1,1,2,3-tetrachloropropene is purified using chromatography, such as HPLC and column chromatography. Again, the instant invention is not so limiting and may include other purification methods such as a liquid-liquid extraction, which may be used alone or in combination with other extraction methods.

The first fluorination reaction, according to the present invention, may be carried out under atmospheric pressure. In another embodiment, this reaction may be carried out under pressures of less than or greater than atmospheric pressures. For example, the process may be carried out, in one embodiment at a pressure ranging from about 0 psig to about 200 psig and in another embodiment, from about 0 psig to about 200 psig and in another embodiment from about 5 psia to about 100 psia.

The first fluorination reaction is conducted under condition effective for the conversion of 1230xfa to 1233xf. In an embodiment, the temperature of the process may range from about 150° C. to about 400° C., in another embodiment from about 180° C. to about 400° C. In another embodiment, the temperature of the process ranges from about 180° C. to about 400° C., while in another embodiment, the temperature of the process is conducted from about 200° C. to about 300° C.

When the compound of formula I is 1230xa, the mol ratio of HF to 1230xa in step 1 of the reaction ranges from about 1:1 to about 50:1 and, in certain embodiments, from about 10:1 to about 20:1. The reaction between HF and 1230xa is carried out at a temperature from about 150° C. to about 400° C. (in certain embodiments, about 180° C. to about 300° C.) and at a pressure of about 0 psig to about 200 psig (in certain embodiments from about 5 psig to about 100 psig). Contact time of the 1230xa with the catalyst may range from about 1 second to about 60 seconds, however, longer or shorter times can be used.

The fluorination reaction is preferably carried out to attain a conversion of about 50% or, preferably, about 90% or higher. Conversion is calculated by the number of moles of reactant (1230xa) consumed divided by number of moles of reactant (1230xa) fed to the reactor multiplied by 100. The selectivity for 1233xf attained is preferably about 60% or higher and more preferably about 80% or higher. Selectivity is calculated by number of moles of product (1233xf) formed divided by number of moles of reactant consumed.

This first step of the reaction may be conducted in any reactor suitable for a vapor phase fluorination reaction. In certain embodiments, the reactor is constructed from materials which are resistant to the corrosive effects of hydrogen fluoride and catalyst such as Hastalloy, Nickel, Incoloy, Inconel, Monel and fluoropolymer linings. The vessel is a fixed catalyst bed or fluidized bed. If desired, inert gases such as nitrogen or argon may be employed in the reactor during operation.

The process may also be monitored based on the consistency of the product produced. For example, if the process results in a product comprising about 95% (w/w) of the product stream, the product stream may be monitored to determine when the percentage of the product in the product stream drops below a pre-determined level. In at least one embodiment, the process may be run continuously until the amount of the desired product in the product stream deviates by more than about 5% (w/w) or by more than about 2% (w/w) in another embodiment. The deviation may be measured over a set period of time to account for short-term changes in the process. For example, the deviation may be measured over a period of time, such as, for example, about 2 minutes, or longer times, such as, for example, about one hour. One skilled in the art would recognize that how the deviation is measured would depend on the desired product purity and consistency. When greater consistency is desired, the allowable deviation may be a small percentage measured over a short period of time. When consistency is not as important, the allowable deviation may be a larger percentage measured over a longer period of time.

The catalyst used in accordance with the process may be activated using any known method. For example, the catalyst may be activated at an elevated temperature in the presence of hydrogen fluoride.

In embodiments in accordance of the present invention, the catalyst may have an extended lifetime compared to reactions in which starting materials comprising higher levels of impurities are used. For example, the catalyst may have a lifetime of at least two times greater than when low purity starting materials are used. In at least some embodiments, the catalyst may last more than three times longer than when low purity starting materials are used.

In an embodiment, the process may be run continuously for at least 100 hours without the need to reactivate or replace the catalyst. In further embodiments, the process may be run continuously for at least 150 hours (or more) without the need to reactivate or replace the catalyst. One of ordinary skill in the art would recognize that longer run times are also within the scope of the present process for the first fluorination step. The actual run time varies, and is determined by several factors, such as the desired product. In an embodiment, the process is monitored at predetermined times and samples removed from the reactor and analyzed using techniques known in the art, such as GC or GC/MS and the like to determine the amount of reactants, products, and the like present therein and results compared to previous samples removed at earlier times to determine amount of change in the % conversion and % selectivity. The need to reactivate or replace the catalyst, or the degree of degradation and/or deactivation, may be determined by a decrease in the conversion of the starting material or a drop in the production of the final product.

According to at least one embodiment, the need to replace or reactivate catalyst may be determined by how long the process may run continuously until less than 85% of the starting material (e.g., HCO-1230xa) is converted. In further embodiments, the process may be run continuously until about 90% or about 95% of the starting material is converted. One of ordinary skill in the art would recognize when to replace or reactivate the catalyst based on the reactor conditions, the desired purity of the product, the difficulty in removing impurities from the product, and the like. For some processes, a higher amount of impurities in the product may be acceptable, whereas in other processes, a low amount of the product is desirable.

In other embodiments, the need to replace or reactivate the catalyst may be based on the amount of product is produced by the process, For example, the process may run continuously until the percentage of product produced (yield or % conversion) drops below about 85%. In other embodiments, the process may be run continuously until the percentage of product produced drop below about 90% or about 95%. One of ordinary skill in the art would recognize that the need to replace or reactivate the catalyst depends on the desired purity of the product and therefore can be adjusted accordingly.

In yet other embodiments, in accordance with the present invention, the need to replace or reactivate the catalysts may be based on the presence of intermediate products in the product stream. The presence of intermediates may indicate that the activity of the catalyst has decreased. For example, in the production of HCFO-1233xf from HCO-1230xa, 2,3-dichloro-3,3-difluoropropene (HCFO-1232xf) is produced as an intermediate. In an embodiment, the need to replace or reactivate the catalyst may be based on the amount of HCFO-1232xf that is present. For example, depending on the desired purity of the product, the process may run continuously until HCFO-1232xf comprises more than about 5% (w/w) of the product stream. In other embodiment, the process may run continuously until HCF)-1232xf comprises more than about 10% (w/w) of the product stream. One of ordinary skill in the art would recognize that the percentage of intermediates, such as HCFO-1232xf, may be determined based on the desired product. For example, if higher purity product is desired, then the process may be run until the intermediates comprise a higher percentage of the product stream, such as, for example, about 15% (w/w) of the product stream.

In general, the effluent from the fluorination reaction step, including any intermediate effluents that may be present in multi-stage reactor arrangements, may be processed to achieve desired degrees of separation and/or other processing. For example, in embodiments in which the reactor effluent includes 1233xf, the effluent will generally also include HCl and one or more of HF, 2,3-dichloro-3,3-difluoropropene (1232xf), 1,2-dichloro-3,3,3-trifluoropropene (1223xd), trichlorofluoropropene (1231) isomers, 2-chloro-1,1,1,2-tetrachloropropane (244bb), and unreacted 1230xa. Some portion or substantially all of these components of the reaction product may be recovered from the reaction mixture via any separation or purification method known in the art such as neutralization and distillation. It is expected that unreacted 1230xa and HF could be recycled, completely or partially, to improve the overall yield of the desired 1233xf. 1232xf and any 1231 formed may also be recycled.

Optionally, hydrogen chloride is then recovered from the result of the fluorination reaction. Recovering of hydrogen chloride is conducted by conventional distillation where it is removed from the distillate. Alternatively, HCl can be recovered or removed by using water or caustic scrubbers. When a water extractor is used, HCl is removed as an aqueous solution. When caustic scrubbers are used, HCl is just removed from system as a chloride salt in aqueous solution.

In an embodiment of the present invention, the process may be performed in the absence of a polymerization inhibitor. In other embodiments, a polymerization inhibitor may be added to the reactor. One of ordinary skill in the art would understand how to select the polymerization inhibitor and the amount present in the reactor based on the operating conditions of the reactor and the reactants used.

In an embodiment, the process may be carried out in the absence of supplied oxygen. In another embodiment, supplied oxygen may be fed to the reactor. The supplied oxygen may be in the form of pure oxygen, oxygen mixed with an inert gas or oxygen in air. One of ordinary skill in the art would understand how to provide the proper amount of supplied oxygen based on the operating conditions of the reactor and the reactants used.

In another embodiment, the process may be carried out in the absence of both a polymerization inhibitor and supplied oxygen.

The HCFO-1233xf produced in the first step of the process is further fluorinated and converted to form HFO-1234yf using methods known in the art, such as those described hereinbelow.

In the second step of the process for forming 2,3,3,3-tetrafluoroprop-1-ene, 1233xf is converted to 2-chloro-1,1,1,2-tetrafluoropropane (244bb). In one embodiment, this step may be performed in the liquid phase in a liquid phase reactor, which may be TFE or PFA-lined. Such a process may be performed in a temperature range of about 70-120° C. and about 50-120 psig.

Any liquid phase fluorination catalyst may be used in the invention. A non-exhaustive list includes Lewis acids, transition metal halides, transition metal oxides, Group IVb metal halides, a Group Vb metal halides, or combinations thereof. Non-exclusive examples of liquid phase fluorination catalysts are an antimony halide, a tin halide, a tantalum halide, a titanium halide, a niobium halide, and molybdenum halide, an iron halide, a fluorinated chrome halide, a fluorinated chrome oxide or combinations thereof. Specific non-exclusive examples of liquid phase fluorination catalysts are $SbCl_5$, $SbCl_3$, $SbF_5$, $SnCl_4$, $TaCl_5$, $TiCl_4$, $NbCl_5$, $MoCl_6$, $FeCl_3$, a fluorinated species of $SbCl_5$, a fluorinated species of $SbCl_3$, a fluorinated species of $SnCl_4$, a fluorinated species of $TaCl_5$, a fluorinated species of $TiCl_4$, a fluorinated species of $NbCl_5$, a fluorinated species of $MoCl_6$, a fluorinated species of $FeCl_3$, or combinations thereof. Antimony pentachloride is most preferred.

These catalysts can be readily regenerated by any means known in the art if they become deactivated. One suitable method of regenerating the catalyst involves flowing a stream of chlorine through the catalyst. For example, from about 0.002 to about 0.2 lb per hour of chlorine can be added to the liquid phase reaction for every pound of liquid phase fluorination catalyst. This may be done, for example, for from about 1 to about 2 hours or continuously at a temperature of from about 65° C. to about 100° C.

This second step of the reaction is not necessarily limited to a liquid phase reaction and may also be performed using a vapor phase reaction or a combination of liquid and vapor phases, such as that disclosed in U.S. Published Patent Application No. 20070197842, the contents of which are incorporated herein by reference. To this end, the 1233xf containing feed stream is preheated to a temperature of from about 50° C. to about 400° C., and is contacted with a catalyst and fluorinating agent. Catalysts may include standard vapor phase agents used for such a reaction and fluorinating agents may include those generally known in the art, such as, but not limited to, hydrogen fluoride.

In the third step of 1234yf production, the 244bb is fed to a second vapor phase reactor (dehydrochlorination reactor) to be dehydrochlorinated to make the desired product 2,3,3,3-tetrafluoroprop-1-ene (1234yf). This reactor contains a catalyst that can catalytically dehydrochlorinate HCFC-244bb to make HFO-1234yf.

The catalysts may be metal halides, halogenated metal oxides, neutral (or zero oxidation state) metal or metal alloy, or activated carbon in bulk or supported form. Metal halide or metal oxide catalysts may include, but are not limited to, mono-, bi-, and tri-valent metal halides, oxides and their mixtures/combinations, and more preferably mono-, and bi-valent metal halides and their mixtures/combinations. Component metals include, but are not limited to, $Cr^{3+}$, $Fe^{3+}$, $Mg^{2+}$, $Ca^{2+}$, $Ni^{2+}$, $Zn^{2+}$, $Pd^{2+}$, $Li^+$, $Na^+$, $K^+$, and $Cs^+$. Component halogens include, but are not limited to, $F^-$, $Cl^-$, $Br^-$, and $I^-$. Examples of useful mono- or bi-valent metal halide include, but are not limited to, LiF, NaF, KF, CsF, $MgF_2$, $CaF_2$, LiCl, NaCl, KCl, and CsCl. Halogenation treatments can include any of those known in the prior art, particularly those that employ HF, $F_2$, HCl, $Cl_2$, HBr, $Br_2$, HI, and $I_2$ as the halogenation source.

When neutral, i.e., zero valent, metals, metal alloys and their mixtures are used. Useful metals include, but are not limited to, Pd, Pt, Rh, Fe, Co, Ni, Cu, Mo, Cr, Mn, and combinations of the foregoing as alloys or mixtures. The catalyst may be supported or unsupported. Useful examples of metal alloys include, but are not limited to, SS 316, Monel 400, Inconel 825, Inconel 600, and Inconel 625.

Preferred, but non-limiting, catalysts include activated carbon, stainless steel (e.g. SS 316), austenitic nickel-based alloys (e.g. Inconel 625), nickel, fluorinated 10% CsCl/MgO, and 10% $CsCl/MgF_2$. The reaction temperature is preferably about 300-550° C. and the reaction pressure may be between about 0-150 psig. The reactor effluent may be fed to a caustic scrubber or to a distillation column to remove the by-product of HCl to produce an acid-free organic product which, optionally, may undergo further purification using one or any combination of purification techniques that are known in the art.

The following are examples of the invention and are not to be construed as limiting.

EXAMPLES

Example 1

This example illustrates the continuous vapor phase fluorination reaction of 1,1,2,3-tetrachloropropene (1230xa) to 2-chloro-3,3,3-trifluoropropene (1233xf). The fluorination catalyst for the experiment was fluorinated $Cr_2O_3$. 1230xa feed used in Example 1 had a purity of 99.2 GC (gas chromatogram) area % and contained 360 ppm of hexachloroethane and ~5000 ppm of tetrachloropropane.

A continuous vapor phase fluorination reaction system consisting of $N_2$, HF, and organic feed systems, feed vaporizer, superheater, 2 inch ID Monel reactor, acid scrubber, drier, and product collection system was used to study the reaction. The reactor was loaded with 1.8 liters of catalyst. The reactor was then heated to a temperature of about 180° C. with a $N_2$ purge going over the catalyst after the reactor had been installed in a constant temperature sand bath. HF feed was introduced to the reactor (via the vaporizer and superheater) as a co-feed with the $N_2$ for 15 minutes when the $N_2$ flow was stopped. The HF flow rate was adjusted to 1.9 lb/hr and then 1,1,2,3-tetrachloropropene (1230xa) feed was started to the reactor (via the vaporizer and superheater). The feed rate of 1230xa was kept steady at 1.0 lb/hr and HF feed was kept steady at 1.9 lb/hr for about a 17 to 1 mole ratio of HF to 1230xa. Once the reaction started the catalyst bed temperature rose to about 200° C. The reaction temperature was gradually increased as catalyst deactivation occurred to maintain desired product collection rate, and reaction was stopped once the reaction temperature reached 300° C. The reaction pressure was kept constant at 70 prig during the entire course of reaction. The reaction was continuously run for about 588 hours and 192 lb of 1233xf and 1232xf was produced. The average conversion of 1230xa and the average selectivity to 1233xf were 69.4%, and 87.3%, respectively.

Example 2

All were the same as in Example 1 except a purer 1230xa was used in Example 2. 1230xa feed used in Example 2 had a purity of 99.7 GC (gas chromatogram) area % and contained 77 ppm of hexachloroethane and no tetrachloropropane. The reaction was continuously run for about 1378 hours and 693 lb of 1233xf and 1232xf was produced. The average conversion of 1230xa and the average selectivity to 1233xf were 90.3%, and 87.1%, respectively.

Example 3

Example 3 demonstrates a process for the fluorination of approximately 99% pure HCO-1230xa at a temperature of 225° C. 3 cc of a high surface area chrome oxide (BASF) was loaded into a ½ inch Hastelloy® reactor. 6 inches of Hastelloy® ⅛ inch distillation packing was packed on top of the catalyst to form a vaporizing zone. The catalyst was activated with hydrogen fluoride. HCO-1230xa was fed from the top of the reactor at a rate of 0.54 ml/hr together with 18 sccm hydrogen fluoride and 3 sccm nitrogen at 225° C. The stream from the reactor was analyzed by GC and GC-MS. In Examples 3-8, the GC used was an Agilient Technologies 7890A which used helium gas as the carrier gas and which flowed at a rate of 3.7674 ml/min.; the GC contained a HP-5 column, 30 cm long, 0.32 mm diameter, 0.25 µM thickness and the stationary phase packed in the column was 5% phenyl methyl siloxane, and the temperature conditions for separation on the GC was conducted using a temperature program of 50 C. for 5 minutes, then 25 C./min to 200 C. for 50 minutes. FIG. 1 shows the mole percent of HCFO-1233xf and HCFO-1232xf in the product stream as a function over a period of 50 hours. FIG. 1 also shows the amount of unreacted HCO-1230xa remaining in the product stream.

The HCO-1230xa fed to the reactor was analyzed by GC(FID). The results of the HCO-1230xa analysis are shown below in Table 1. Based upon the GC Area, the mol % was determined

TABLE 1

| Compound | GC (FID) Area (%) | Mol % |
|---|---|---|
| HCO-1230xa | 99.02% | 99.22 |
| $CH_2ClCCl_2CH_2Cl$ | 0.94% | 0.72 |
| $C_3H_3Cl_5$ | 0.02% | 0.01 |
| $CCl_3CCl_3$ | 0.02% | 0.03 |
| $C_3HCl_5$ | 0.01% | 0.02 |

Example 4

Figure 2:
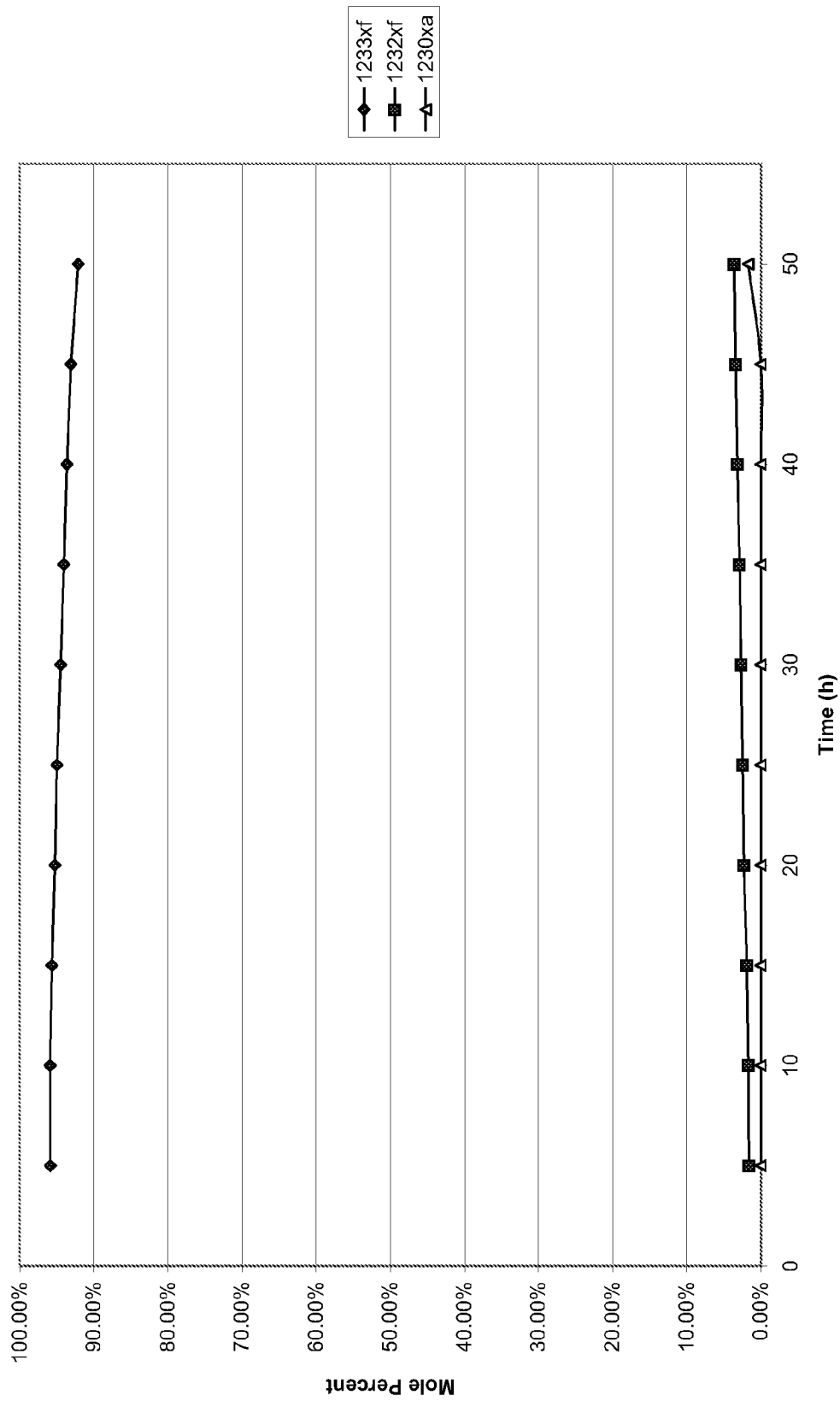
FIG. 2 graphically represents the mole percentage of HCFO-1233xf produced and HCO-1230xa remaining as a function of time resulting from the process conducted in accordance with the procedure of Example 4.
Figure 5:
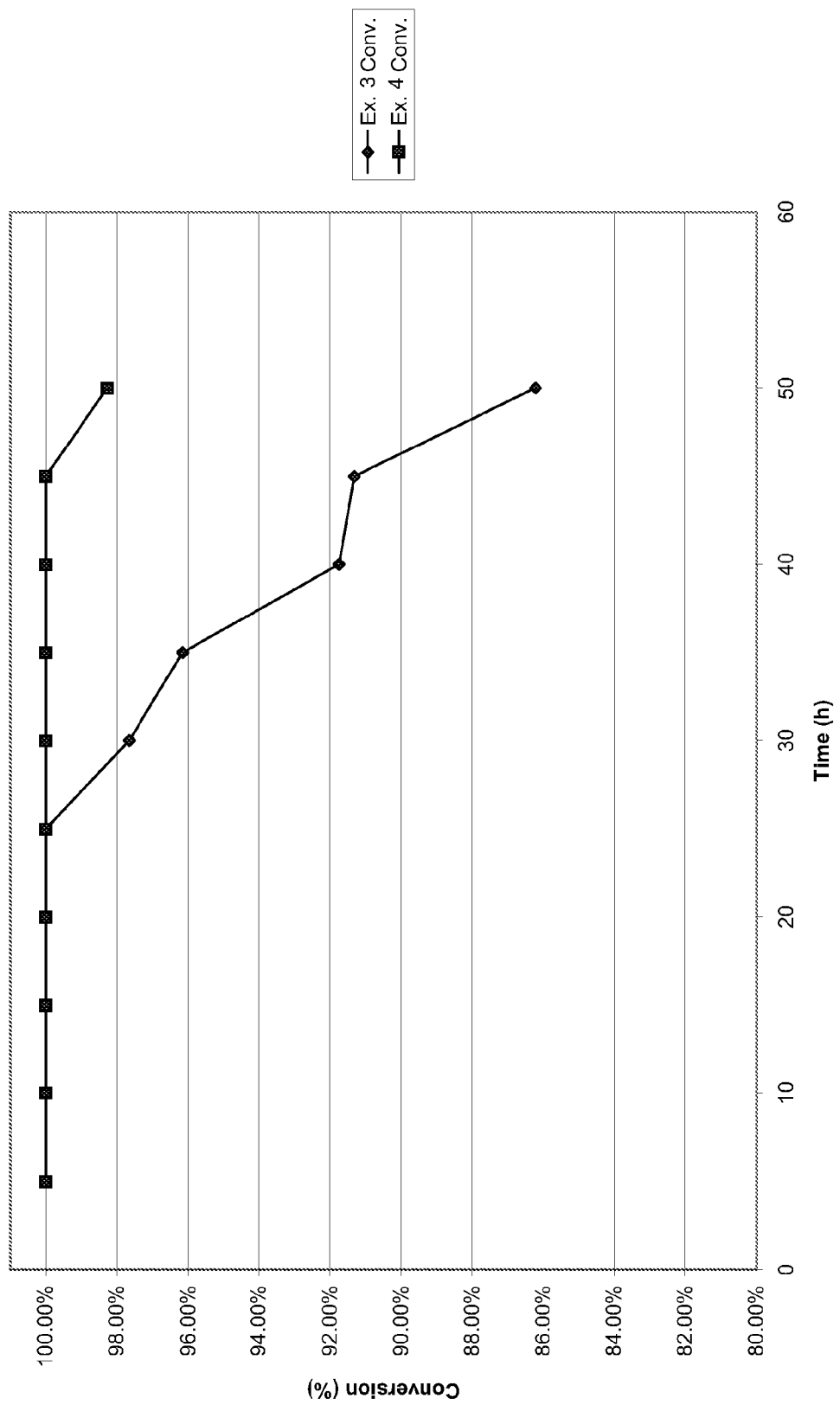
FIG. 5 graphically represents the conversion percentage of HCO-1230xa as a function of time resulting from the process conducted in accordance with the procedure of Examples 3 and 4.

In Example 4, an approximately 99.9% HCO-1230xa was used as the starting material for the fluorination reaction. 3 cc of a high surface area chrome oxide (BASF) was loaded into a ½ inch Hastelloy® reactor. 6 inches of Hastelloy® ⅛ inch distillation packing was packed on top of the catalyst to form a vaporizing zone. The catalyst was activated with hydrogen fluoride. HCO-1230xa was fed from the top of the reactor at a rate of 0.54 ml/hr together with 18 sccm hydrogen fluoride and 3 sccm nitrogen at 225° C. The stream from the reactor was analyzed by GC and GC-MS. FIG. 2 shows the mole percent of HCFO-1233xf and HCFO-1232xf in the product stream as a function over a period of 50 hours. FIG. 2 also shows the amount of unreacted HCO-1230xa present in the product stream. FIG. 5 shows the percentage of HCO-1230xa converted (i.e., the percentage of HCO-1230xa that reacted) in Examples 3 and 4.

GC analysis of the HCO-1230xa used in Example 4 is shown below in Table 2. Based upon the GC Area, the mol % was determined.

TABLE 2

| Compound | GC (FID) Area (%) | Mol % |
|---|---|---|
| HCO-1230xa | 99.90% | 99.92% |
| $CH_2ClCH=CCl_2$ | 0.06% | 0.05% |
| $CHCl_2CCl=CHCl$ | 0.04% | 0.03% |

Example 5

Figure 3:
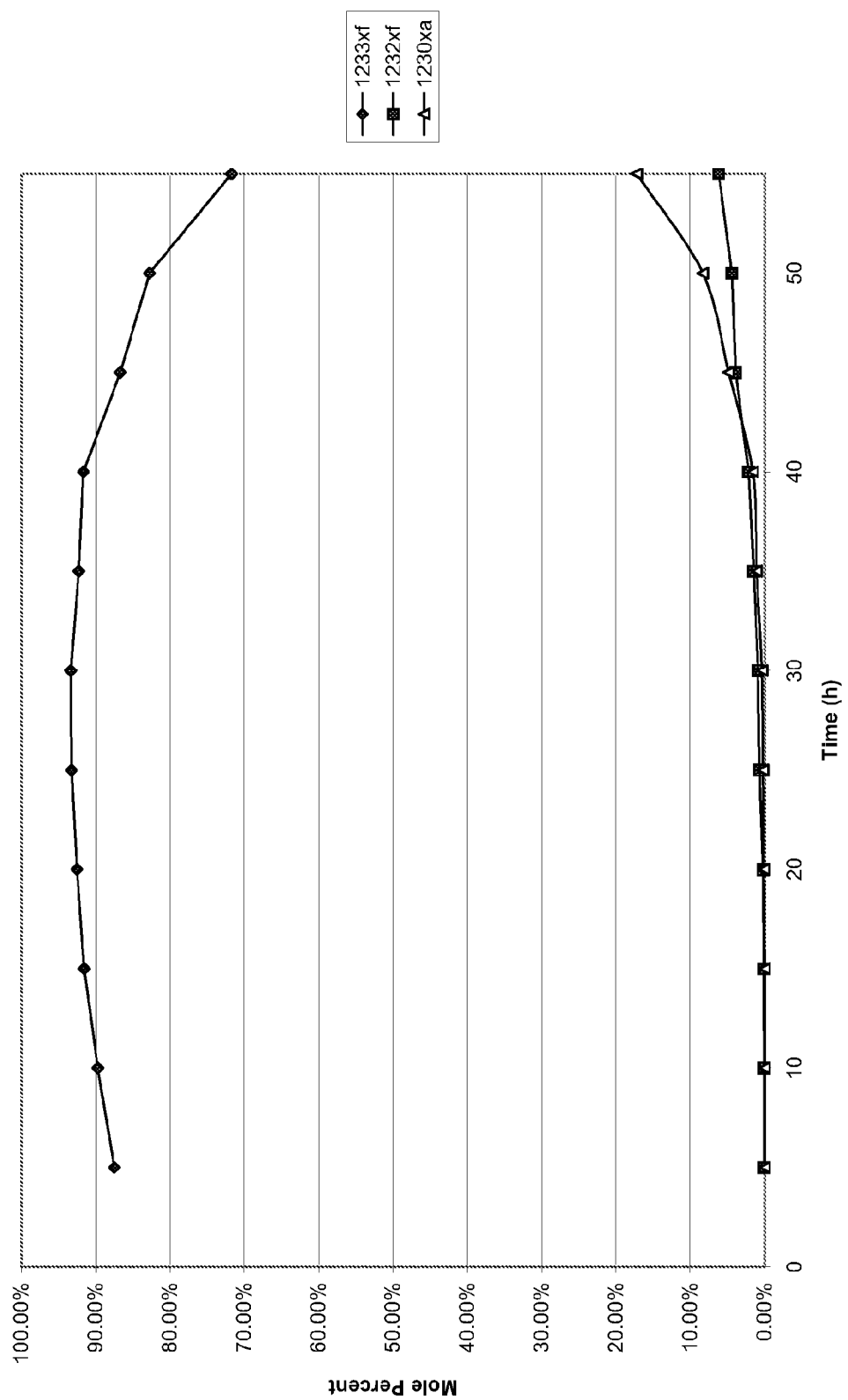
FIG. 3 graphically represents the mole percentage of HCFO-1233xf produced and HCO-1230xa remaining as a function of time resulting from the process conducted in accordance with the procedure of Example 5.

In Example 5, the process used the same HCO-1230xa used above in Example 3. 3 cc of a high surface area chrome oxide (BASF) was loaded into a ½ inch Hastelloy® reactor. 6 inches of Hastelloy® ⅛ inch distillation packing was packed on top of the catalyst to form a vaporizing zone. The catalyst was activated with hydrogen fluoride. HCO-1230xa was fed from the top of the reactor at a rate of 0.54 ml/hr together with 18 sccm hydrogen fluoride and 3 sccm nitrogen at 275° C. The stream from the reactor was analyzed by GC and GC-MS. FIG. 3 shows the mole percent of HCFO-1233xf and HCFO-1232xf in the product stream as a function over a period of 55 hours. FIG. 3 also shows the amount of unreacted HCO-1230xa present in the product stream.

Example 6

Figure 4:
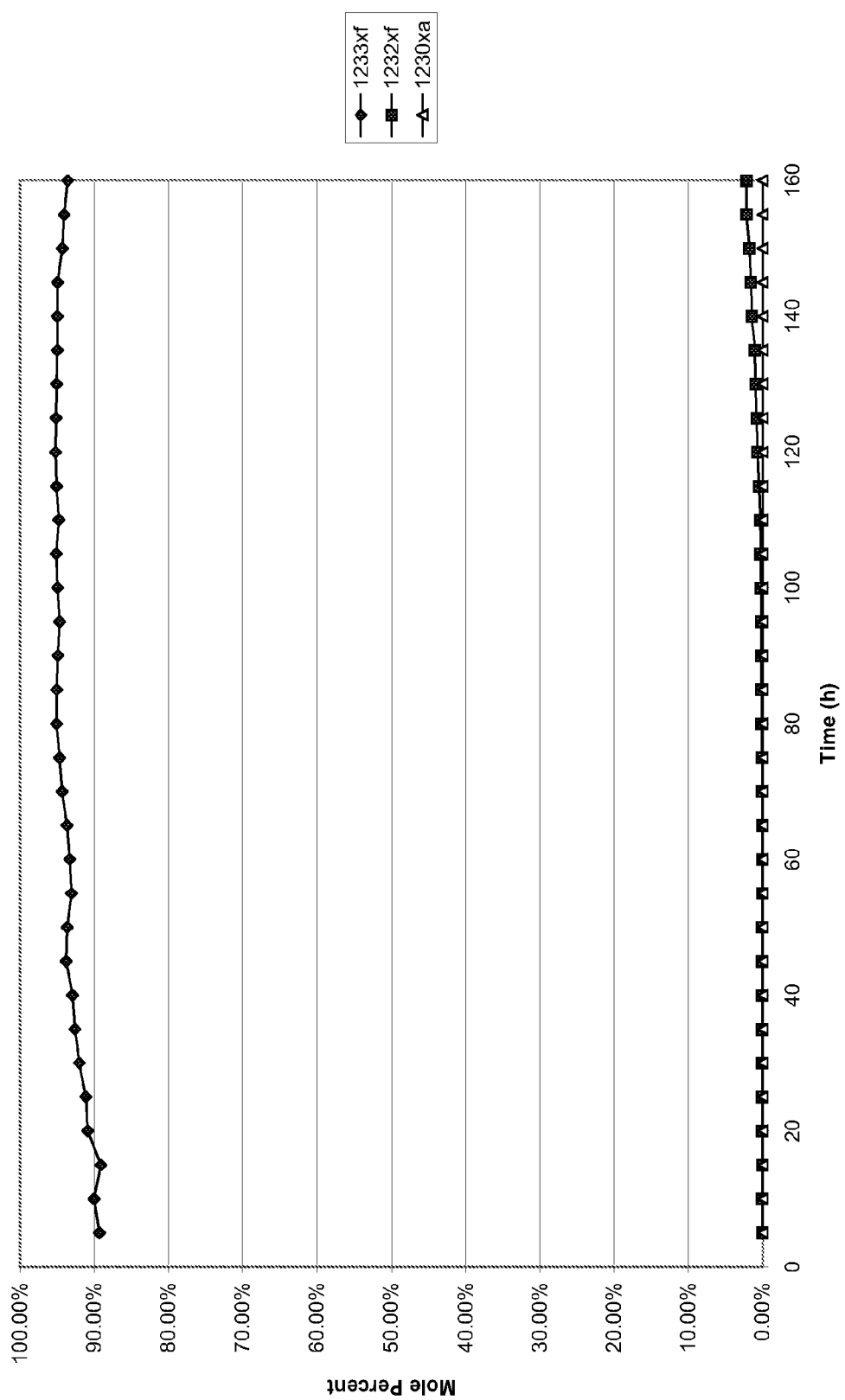
FIG. 4 graphically represents the mole percentage of HCFO-1233xf produced and HCO-1230xa remaining as a function of time resulting from the process conducted in accordance with the procedure of Example 6.

Example 6 used the HCO-1230xa feed as described above in Example 4. 3 cc of a high surface area chrome oxide (BASF) was loaded into a ½ inch Hastelloy® reactor. 6 inches of Hastelloy® ⅛ inch distillation packing was packed on top of the catalyst to form a vaporizing zone. The catalyst was activated with hydrogen fluoride. HCO-1230xa was fed from the top of the reactor at a rate of 0.54 ml/hr together with 18 sccm hydrogen fluoride and 3 sccm nitrogen at 275° C. The stream from the reactor was analyzed by GC and GC-MS. FIG. 4 shows the mole percent of HCFO-1233xf and HCFO-1232xf in the product stream as a function over a period of 160 hours. FIG. 4 also shows the amount of unreacted HCO-1230xa present in the product stream.

Figure 6:
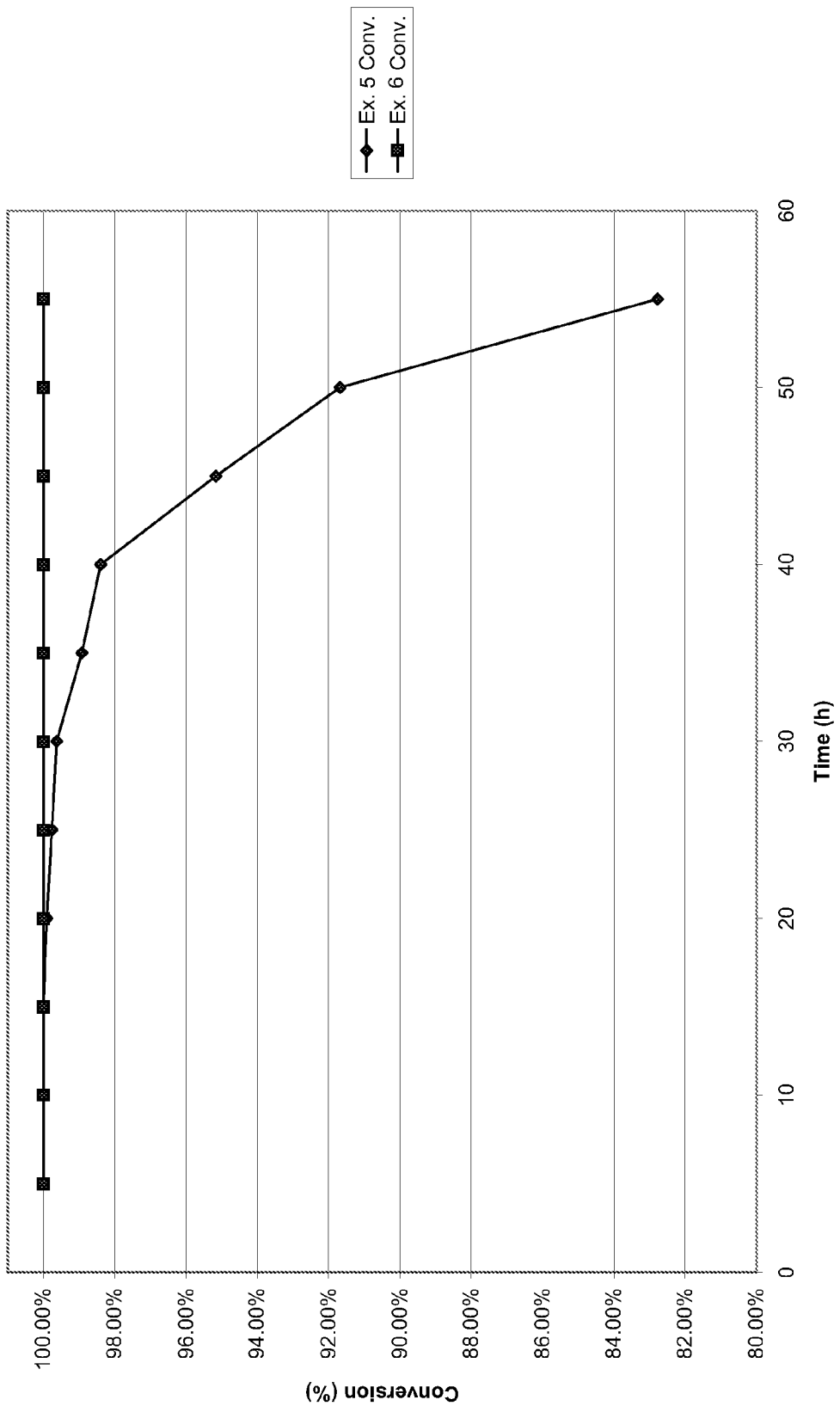
FIG. 6 graphically represents the conversion percentage of HCO-1230xa over a period of 55 hours when the process was conducted in accordance with the procedure of Examples 5 and 6.
Figure 7:
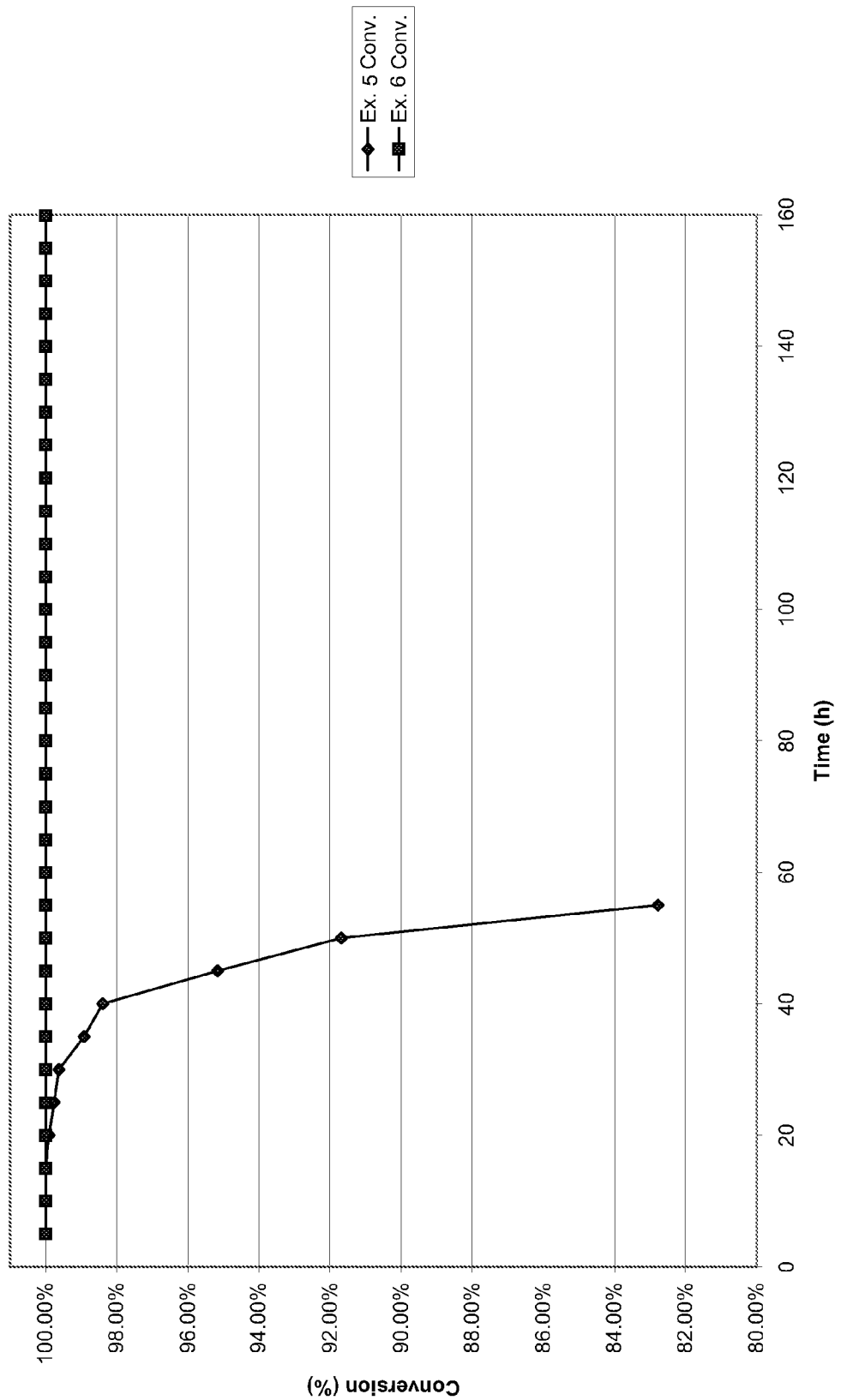
FIG. 7 graphically represents the conversion percentage of HCO-1230xa over a period of 160 hours when the process was conducted in accordance with the procedure of Examples 5 and 6.

FIGS. 6 and 7 show the amount of HCO-1230xa reacted in Examples 5 and 6 at times up to 50 hours and 160 hours, respectively.

Example 7

Figure 8:
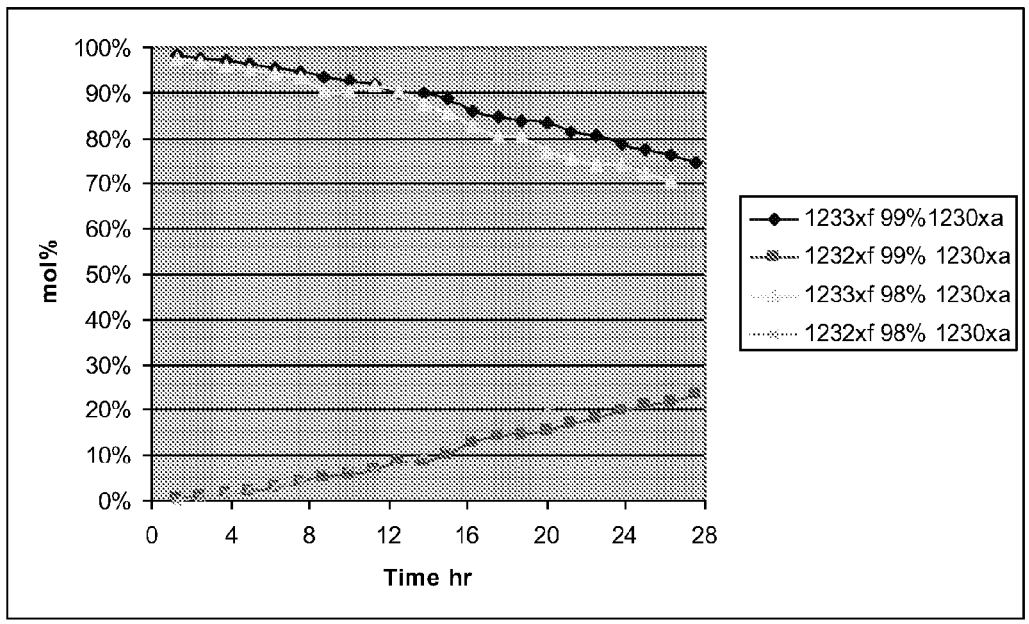
FIG. 8 graphically represents the mole percentage of HCFO-1233xf in the product stream as a function of time over a period of 28 hours resulting from the process conducted in accordance with the procedure of Example 8.
Figure 9:
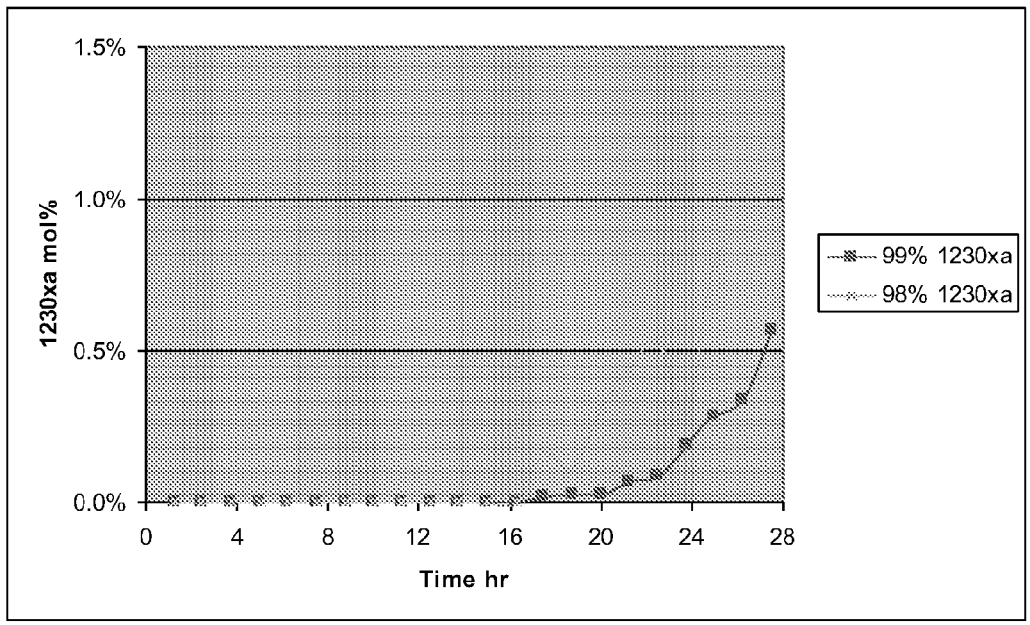
FIG. 9 graphically shows the amount of unreacted HCFO-1230xa present in the product stream after the process was conducted in accordance with the procedure of Example 8.

In Example 7, 1% 250 fb was added into the 99% pure 1230xa (as shown in table 1). Then this approximately 98% HCO-1230xa was used as the starting material for the fluorination reaction. 2.15 cc of a high surface area chrome oxide E410 (BASF) was loaded into a ½ inch Hastelloy® reactor. 6 inches of Hastelloy® ⅛ inch distillation packing was packed on top of the catalyst to form a vaporizing zone. The catalyst was activated with hydrogen fluoride. HCO-1230xa was fed from the top of the reactor at a rate of 0.54 ml/hr together with 18 sccm hydrogen fluoride and 6 sccm nitrogen at 225° C. The stream from the reactor was analyzed by GC and GC-MS. FIG. 8 shows the mole percent of HCFO-1233xf and HCFO-1232xf in the product stream as a function over a period of 28 hours. FIG. 9 also shows the amount of unreacted HCO-1230xa present in the product stream.

Example 8

In Example 8, 99% pure 1230xa (as shown in table 1) was used as the starting material for the fluorination reaction. 2.15 cc of a high surface area chrome oxide E410 (BASF) was loaded into a ½ inch Hastelloy® reactor. 6 inches of Hastelloy® ⅛ inch distillation packing was packed on top of the catalyst to form a vaporizing zone. The catalyst was activated with hydrogen fluoride. HCO-1230xa was fed from the top of the reactor at a rate of 0.54 ml/hr together with 18 sccm hydrogen fluoride and 6 sccm nitrogen at 225° C. The stream from the reactor was analyzed by GC and GC-MS. FIG. 8 shows the mole percent of HCFO-1233xf and HCFO-1232xf in the product stream as a function over a period of 28 hours. FIG. 9 also shows the amount of unreacted HCO-1230xa present in the product stream. The results shows catalyst with 98% 1230xa lost activist much faster that the catalyst with 99% 1230xa.

The above preferred embodiments and examples were given to illustrate the scope and spirit of the present invention. These embodiments and examples will make apparent to those skilled in the art other embodiments and examples. The other embodiments and examples are within the contemplation of the present invention. Therefore, the present invention should be limited only by the amended claims.

What is claimed is:

1. A feed stock for use in preparing a fluoroolefin comprising a composition comprising 1,1,2,3-tetrachloropropene that is substantially free of impurities, wherein said impurities comprise one or more materials selected from ionic metal, hexachloroethane, tetrachloropropane, pentachloropropane, dichloropropene, trichloropropane, hexachlorohexadiene, trichloropropene, pentachloropropene, dichlorobutene, and combinations thereof.

2. The feed stock of claim 1 wherein less that 1% impurity is present as measured by GC (FID) area.

3. The feed stock of claim 1, wherein the impurity is an ionic metal, wherein the ionic metal is present in the composition in an amount less than about 100 ppm.

4. The feed stock of claim 1, wherein the impurities comprise one or more organic compounds selected from the group consisting of hexachloroethane, tetrachloropropane, pentachloropropane, dichloropropene, trichloropropane, hexachlorohexadiene, trichloropropene, pentachloropropene, dichlorobutene, and combinations thereof.

5. The feed stock of claim 4, wherein any one of the organic compounds is present in the composition in an amount less than 1000 ppm.

6. The feed stock of claim 4, wherein the one or more organic compounds are provided at less than 0.5% (w/w) of the composition.

7. A process for preparing 2-chloro-3,3,3-trifluoropropene comprising:
providing a starting composition comprising at least one compound of formula I $$CX_2=CCl-CH_2X \qquad (I)$$

wherein X is independently selected from F, Cl, Br, and I, provided that at least one X is not fluorine and wherein the starting composition is substantially free of impurities, wherein said impurities comprise one or more materials selected from ionic metal, hexachloroethane, tetrachloropropane, pentachloropropane, di chloropropene, trichloropropane, hexachlorohexadiene, trichloropropene, pentachloropropene, dichlorobutene, and combinations thereof; and
contacting said starting composition with a fluorinating agent to produce a final composition comprising 2-chloro-3,3,3-trifluoropropene.

8. The process of claim 7, wherein at least one compound of formula I is a compound comprising at least one X is a chlorine.

9. The process of claim 7, wherein at least one compound of formula I is a compound where all Xs are chlorine.

10. The process of claim 7, wherein the at least one compound of formula I comprises 1,1,2,3-tetrachloropropene.

11. The process of claim 7, wherein the contacting of said starting composition with a fluorinating agent occurs in a vapor phase.

12. The process of claim 7, wherein the contacting occurs in the presence of a catalyst.

13. The process of claim 12, wherein the catalyst is a vapor phase catalyst.

14. The process of claim 13, wherein the vapor phase catalyst is selected from the group consisting of a chromium oxide, a chromium hydroxide, a chromium halide, a chromium oxyhalide, an aluminum oxide, an aluminum hydroxide, an aluminum halide, an aluminum oxyhalide, a cobalt oxide, a cobalt hydroxide, a cobalt halide, a cobalt oxyhalide, a manganese oxide, a manganese hydroxide, a manganese halide, a manganese oxyhalide, a nickel oxide, a nickel hydroxide, a nickel halide, a nickel oxyhalide, an iron oxide, an iron hydroxide, an iron halide, an iron oxyhalide, inorganic salts thereof, fluorinated derivatives thereof and combinations thereof.

15. The process of claim 14 wherein the catalyst comprises a chromium oxide.

16. The process of claim 7 wherein less than 1% impurity is present as measured by GC area.

17. The process of claim 7, wherein the impurity is an ionic metal, wherein the ionic metal is present in the composition in an amount less than about 100 ppm.

18. The process of claim 7, wherein the impurities comprise one or more organic compounds selected from the group consisting of hexachloroethane, tetrachloropropane, pentachloropropane, dichloropropene, trichloropropene, trichloropropane, hexachlorohexadiene, pentachloropropene, dichlorobutene, and combinations thereof.

19. The process of claim 18, wherein any one of the organic compounds is present in the composition in an amount less than 1000 ppm.

20. The process of claim 18, wherein the one or more organic compounds are collectively present in a concentration of less than 0.5% (w/w) of the composition.

21. The process of claim 7 wherein contacting the composition with hydrogen fluoride is conducted in the absence of supplied oxygen and/or in the absence of a polymerization inhibitor.

22. The process of claim 7 wherein contacting the composition with hydrogen is conducted in the presence of supplied oxygen and/or in the presence of a polymerization inhibitor.

23. The process of claim 15 where the catalyst has a surface area ranging from about 60 m²/g to about 300 m²/g.

24. The process of claim 7 wherein contacting the starting composition with hydrogen fluoride is conducted at a temperature ranging from about 180° C. to about 400° C.

25. The process of claim 7 wherein contacting the starting composition with hydrogen fluoride is conducted at a pressure ranging from about 5 psia to about 100 psia.

26. A process for preparing 2,3,3,3-tetrafluoroprop-1-ene comprising:
providing a starting composition comprising a compound of formula I $$CX_2=CCl-CH_2X \qquad (I)$$

wherein X is independently selected from F, Cl, Br, and I, provided that at least one X is not fluorine and the starting composition is substantially free of impurities, wherein said impurities comprise one or more materials selected from ionic metal, hexachloroethane, tetrachloropropane, pentachloropropane, dichloropropene, trichloropropane, hexachlorohexadiene, trichloropropene, pentachloropropene, dichlorobutene, and combinations thereof;

contacting said starting composition with a first fluorinating agent to produce a first intermediate composition comprising 2-chloro-3,3,3-trifluoropropene;

contacting said first intermediate composition with a second fluorinating agent to produce a second intermediate composition comprising 2-chloro-1,1,1,2-tetrafluoropropane; and dehydrochlorinating at least a portion of said 2-chloro-1,1,1,2-tetrafluoropropane to produce a reaction product comprising 2,3,3,3-tetrafluoroprop-1-ene.

27. A feed stock for use in preparing a fluoroolefin according to claim 1 comprising a composition comprising 1,1,2,3-tetrachloropropene that is substantially free of impurities, wherein said impurities comprise one or more materials selected from ionic metal, hexachloroethane, tetrachloropropane, pentachloropropane, trichloropropane, and combinations thereof.

28. The process according to claim 7 wherein the starting composition is substantially is substantially free of impurities, wherein the impurities comprise one or more materials selected from ionic metal, hexachloroethane, tetrachloropropane, pentachloropropane, trichloropropane, and combinations thereof.

29. The process according to claim 26 wherein the starting is substantially free of impurities wherein said impurities comprise one or more materials selected from ionic metal, hexachloroethane, tetrachloropropane, pentachloropropane, trichloropropane, and combinations thereof.

\* \* \* \* \*